United States Patent
Jaryal et al.

(10) Patent No.: US 8,609,854 B2
(45) Date of Patent: Dec. 17, 2013

(54) PROCESS FOR THE PREPARATION OF SORAFENIB TOSYLATE

(75) Inventors: Jagdev Singh Jaryal, Kangra (IN); Swargam Sathyanarayana, Karim Nagar (IN); Rajesh Kumar Thaper, Jammu (IN); Mohan Prasad, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 13/497,835

(22) PCT Filed: Sep. 24, 2010

(86) PCT No.: PCT/IB2010/054323
§ 371 (c)(1),
(2), (4) Date: May 9, 2012

(87) PCT Pub. No.: WO2011/036647
PCT Pub. Date: Mar. 31, 2011

(65) Prior Publication Data
US 2013/0005980 A1    Jan. 3, 2013

(30) Foreign Application Priority Data
Sep. 24, 2009 (IN) .......................... 2007/DEL/2009

(51) Int. Cl.
*C07D 213/63* (2006.01)
*C07D 213/70* (2006.01)
*A61K 31/44* (2006.01)

(52) U.S. Cl.
USPC .......................................... 546/291; 514/346

(58) Field of Classification Search
CPC ..... C07D 213/63; C07D 213/70; A61K 31/44
See application file for complete search history.

(56) References Cited

FOREIGN PATENT DOCUMENTS

| WO | WO 00/42012 | 7/2000 |
|---|---|---|
| WO | WO 2006/034796 | 4/2006 |
| WO | WO 2006/034796 A1 * | 4/2006 |
| WO | WO 2006/034797 | 4/2006 |
| WO | WO 2006034796 A1 * | 4/2006 |
| WO | WO 2009/034308 | 3/2009 |
| WO | WO 2009/054004 | 4/2009 |
| WO | WO 2009/092070 | 7/2009 |
| WO | WO 2009/092070 A1 * | 7/2009 |
| WO | WO 2009/106825 | 9/2009 |

OTHER PUBLICATIONS

Zhao, C. et al. Synthesis of sorafenib tosylate. Zhongguo Yiyao Gongye Zazhi. 2007, vol. 38(9), p. 614-616 (STN translation reaction #1 of 24).*

Hyeon, T. et al. Designed Synthesis of Atom-Economical Pd/Ni Bimetallic Nanoparticle-Based Catalysts for Sonogashira Coupling Reactions. J. Am. Chem. Soc. 2004, vol. 126, p. 5026, table 1.*

* cited by examiner

*Primary Examiner* — Rita Desai
*Assistant Examiner* — Ben S Michelson

(57) ABSTRACT

The present invention provides a process for the preparation of sorafenib tosylate, comprising contacting sorafenib free base with p-toluenesulphonic acid in water.

8 Claims, 4 Drawing Sheets

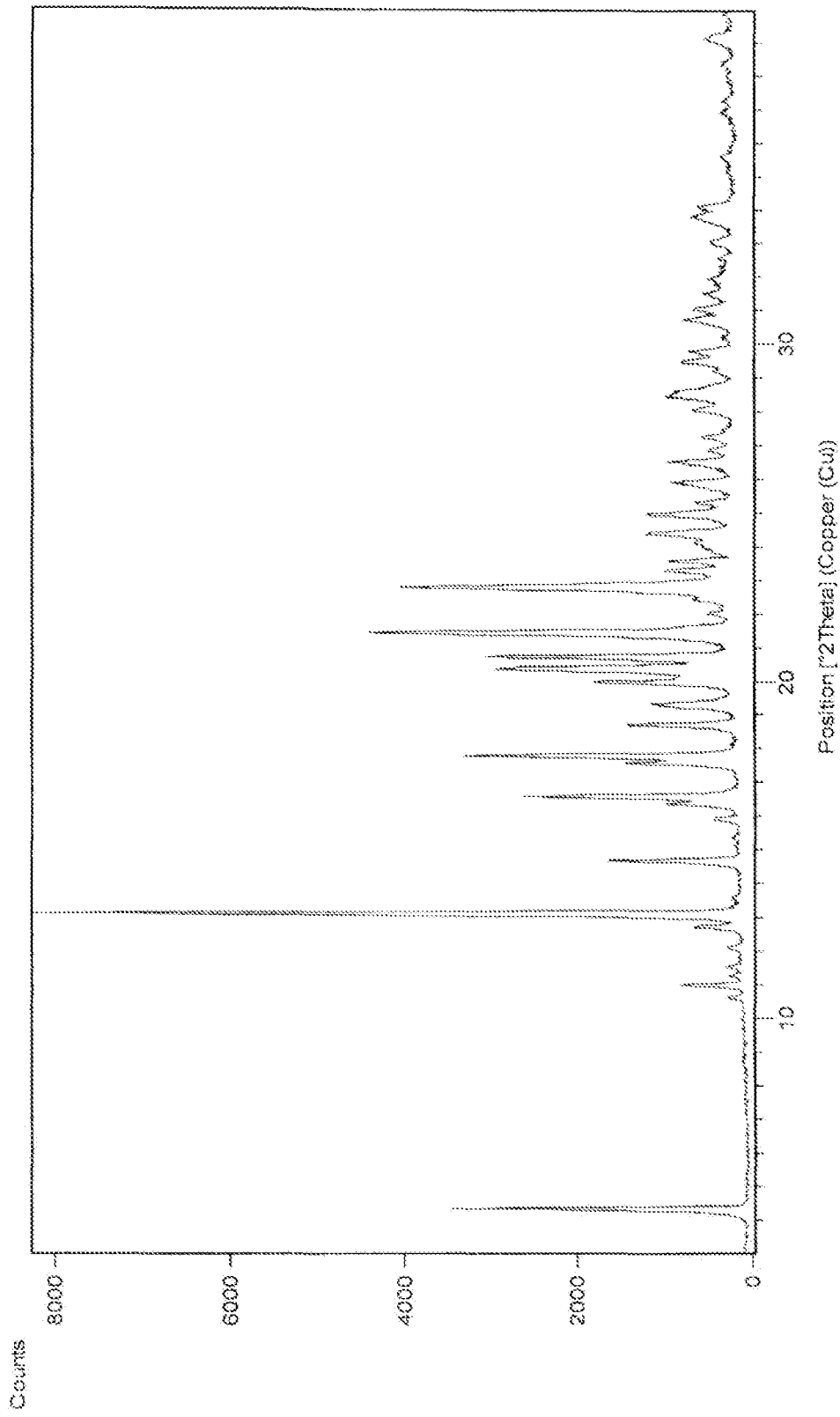
FIG. 1 - XRD Pattern of Sorafenib Tosylate

FIG. 1A: Peak Table for the XRD Pattern Depicted in Figure 1

| Position (°2θ) | d-spacing (Å) | Relative Intensity (%) |
|---|---|---|
| 4.35 | 20.32 | 24.79 |
| 10.63 | 8.32 | 1.52 |
| 11.02 | 8.03 | 6.72 |
| 11.28 | 7.84 | 1.31 |
| 11.57 | 7.65 | 1.80 |
| 12.15 | 7.28 | 1.69 |
| 12.76 | 6.94 | 5.73 |
| 13.15 | 6.73 | 89.17 |
| 13.61 | 6.50 | 2.04 |
| 14.71 | 6.02 | 16.42 |
| 15.94 | 5.56 | 3.68 |
| 16.36 | 5.42 | 5.81 |
| 16.59 | 5.34 | 27.31 |
| 17.56 | 5.05 | 11.50 |
| 17.79 | 4.98 | 33.20 |
| 18.72 | 4.74 | 15.52 |
| 19.35 | 4.59 | 6.71 |
| 19.99 | 4.44 | 17.28 |
| 20.35 | 4.36 | 48.85 |
| 20.43 | 4.35 | 29.61 |
| 20.74 | 4.28 | 59.78 |
| 21.45 | 4.14 | 100.00 |
| 22.01 | 4.04 | 4.61 |
| 22.42 | 3.96 | 7.14 |
| 22.78 | 3.90 | 80.64 |
| 23.28 | 3.82 | 14.96 |
| 23.59 | 3.77 | 10.76 |
| 24.45 | 3.64 | 24.53 |
| 24.94 | 3.57 | 19.22 |
| 25.29 | 3.52 | 5.42 |
| 25.91 | 3.44 | 9.46 |
| 26.50 | 3.36 | 8.68 |
| 26.87 | 3.32 | 6.44 |
| 27.24 | 3.27 | 7.38 |
| 28.04 | 3.18 | 7.91 |
| 28.44 | 3.14 | 16.82 |
| 29.47 | 3.03 | 16.03 |
| 29.77 | 3.00 | 8.55 |
| 30.72 | 2.91 | 17.70 |
| 31.05 | 2.88 | 12.37 |
| 31.48 | 2.84 | 7.64 |
| 31.93 | 2.80 | 8.14 |
| 33.05 | 2.71 | 10.02 |
| 33.80 | 2.65 | 13.18 |
| 34.11 | 2.63 | 9.54 |
| 35.60 | 2.52 | 4.01 |
| 36.92 | 2.43 | 4.55 |
| 38.34 | 2.34 | 4.48 |
| 39.11 | 2.30 | 10.15 |

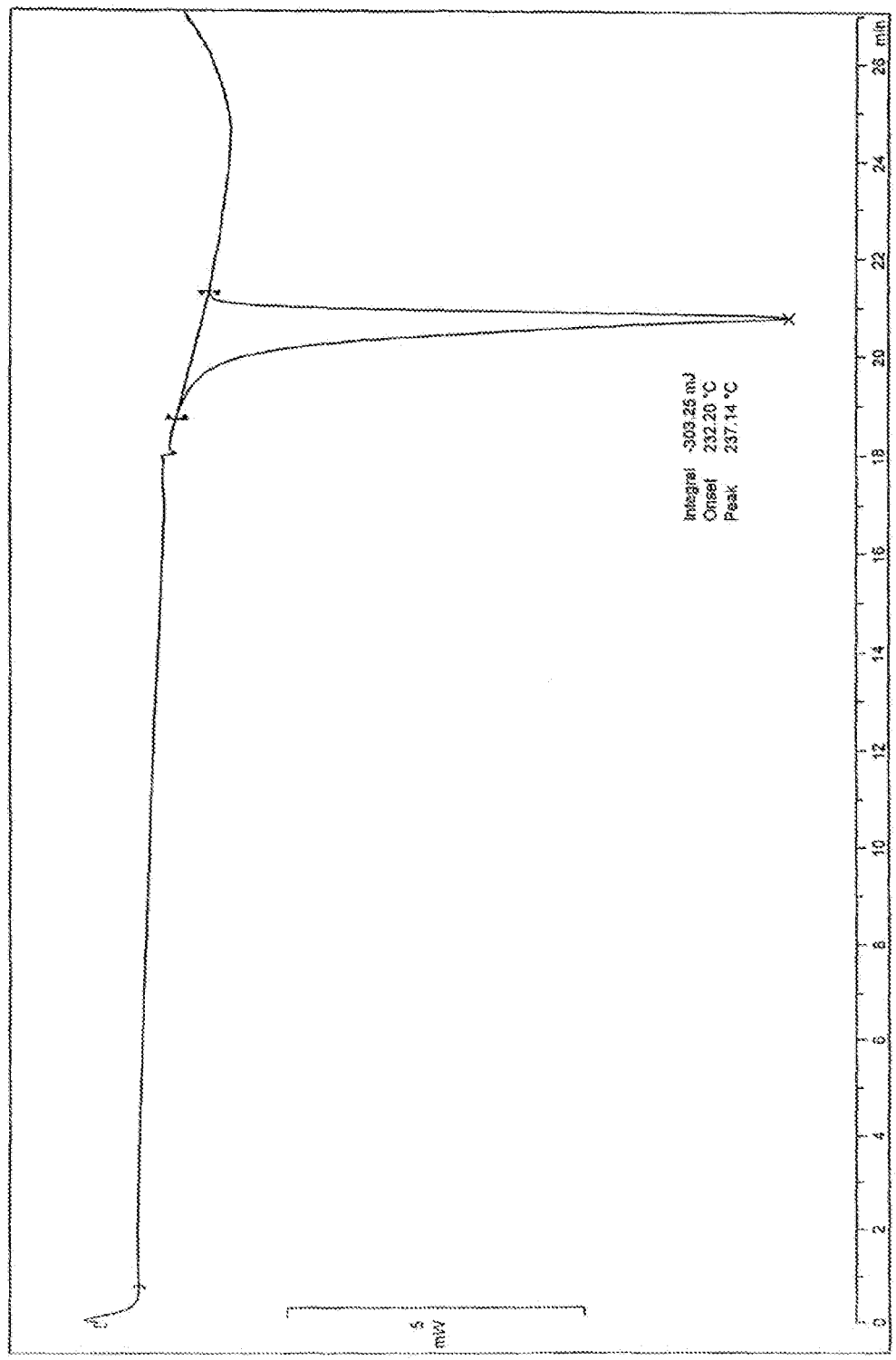
FIG. 2: DSC Thermogram of Sorafenib Tosylate

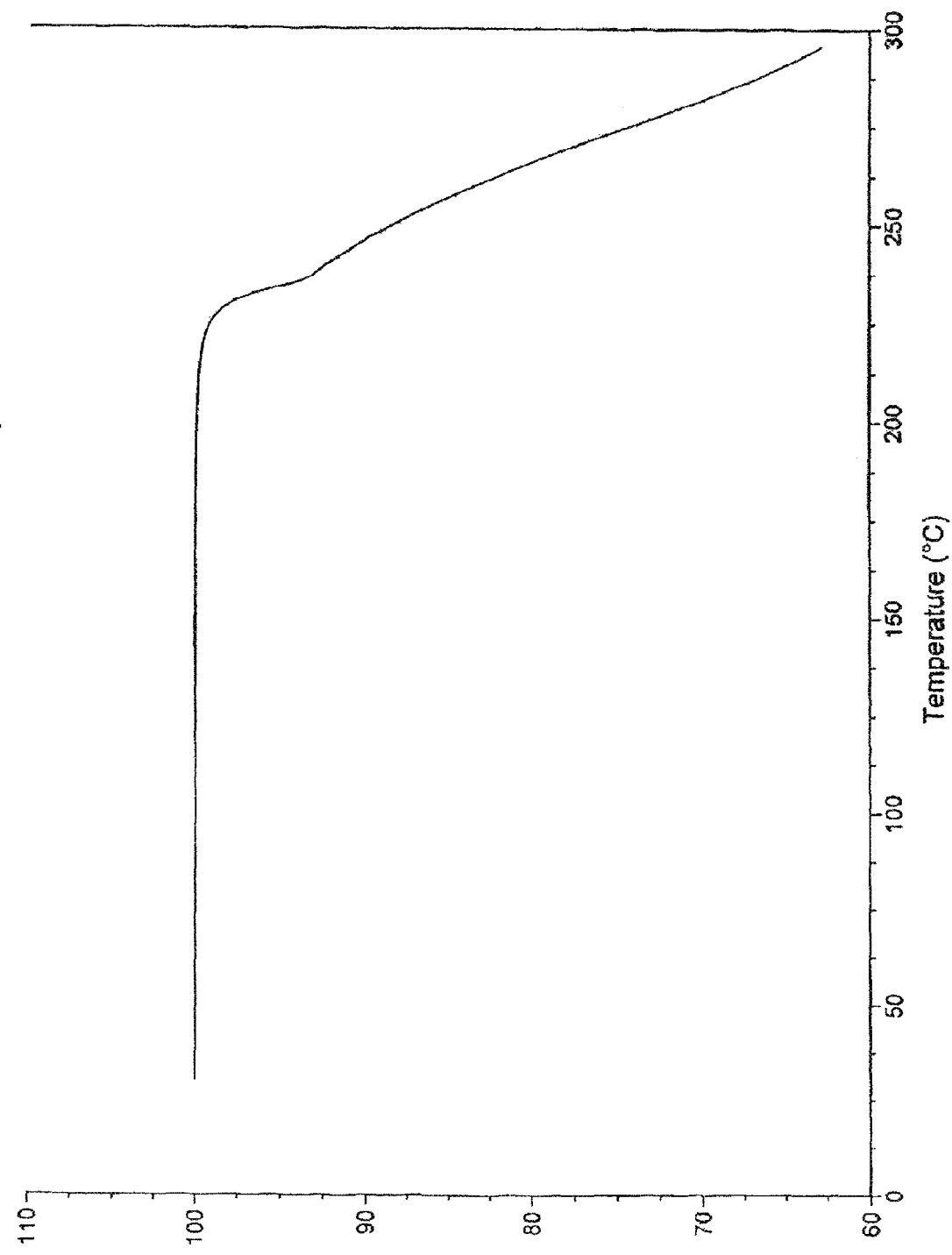
Figure 3: TGA Curve of Sorafenib Tosylate

PROCESS FOR THE PREPARATION OF SORAFENIB TOSYLATE

FIELD OF THE INVENTION

The present invention provides a process for the preparation of sorafenib tosylate.

BACKGROUND OF THE INVENTION

Sorafenib tosylate is the tosylate salt of 4-(4-{3-[4-chloro-3-(trifluoromethyl) phenyl]ureido}phenoxy)-$N^2$-methylpyridine-2-carboxamide, having the structure as represented by Formula I.

FORMULA I

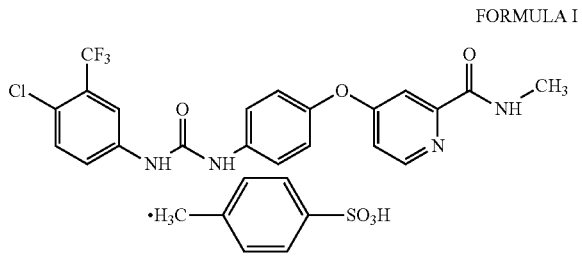

Sorafenib tosylate is an inhibitor of the enzyme rafkinase. It is marketed in the United States under the brand name Nexavar® for the treatment of unresectable hepatocellular carcinoma and advanced renal cell carcinoma.

WO 2006/034796, which is incorporated herein by reference, describes a process for the preparation of sorafenib tosylate in polar solvents.

The use of water, without using any other solvent, for the preparation of sorafenib tosylate is not described in the literature.

SUMMARY OF THE INVENTION

The present inventors have developed a process for the preparation of sorafenib tosylate which involves reaction of sorafenib free base with p-toluenesulphonic acid in water.

A first aspect of the present invention provides a process for the preparation of sorafenib tosylate of Formula I

FORMULA I

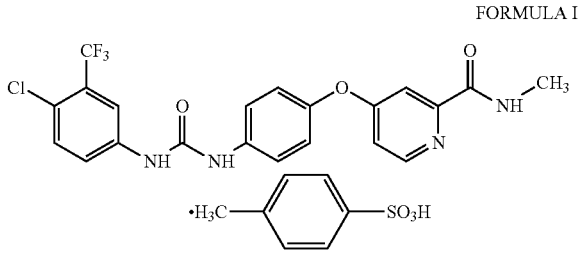

comprising contacting sorafenib free base with p-toluenesulphonic acid in water.

A second aspect of the present invention provides a process for the preparation of sorafenib tosylate of Formula I

FORMULA I

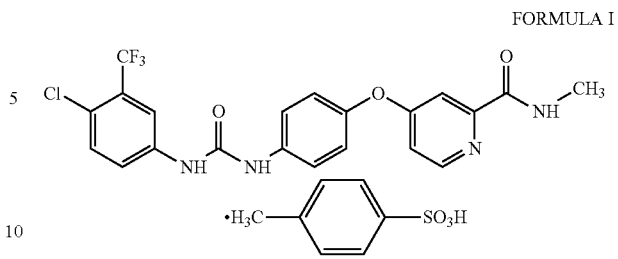

comprising contacting sorafenib free base with p-toluenesulphonic acid in water wherein 1.5 mole equivalents of p-toluenesulphonic acid are added per mole equivalent of sorafenib free base.

A third aspect of the present invention provides a process for the preparation of sorafenib tosylate of Formula I

FORMULA I

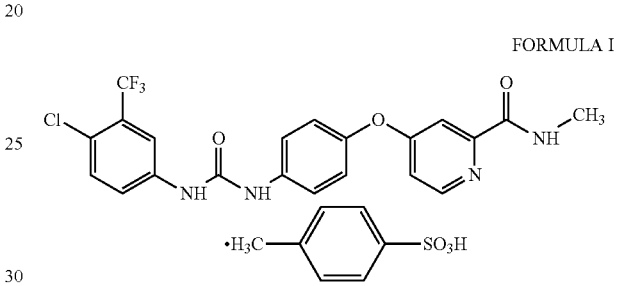

comprising contacting sorafenib free base with p-toluenesulphonic acid in water wherein more than 1.5 mole equivalents of p-toluenesulphonic acid are added per mole equivalent of sorafenib free base.

A fourth aspect of the present invention provides high purity sorafenib tosylate.

BRIEF DESCRIPTION OF THE DRAWINGS

FIG. 1: XRD pattern of sorafenib tosylate prepared by the process of the present invention.

FIG. 2: DSC thermogram of sorafenib tosylate prepared by the process of the present invention.

FIG. 3: TGA curve of sorafenib tosylate prepared by the process of the present invention.

DETAILED DESCRIPTION OF THE INVENTION

Sorafenib free base to be used for the preparation of sorafenib tosylate may be obtained by any of the methods known in the literature such as those described in WO 00/42012, WO 2006/034796, WO 2006/034797, WO 2009/034308, WO 2009/054004, WO 2009/106825 and WO 2009/092070, which are incorporated herein by reference.

In general, sorafenib free base may be prepared by the reaction of 4-(2-(N-methylcarbamoyl)-4-pyridyloxy) aniline with 4-chloro-3-(trifluoromethyl)phenyl isocyanate. The starting sorafenib free base may be obtained as a solution directly from a reaction in which sorafenib is formed and used as such without isolation.

The p-toluenesulphonic acid may be used either in anhydrous form or in the form of hydrates. Preferably, p-toluenesulphonic acid monohydrate may be used.

The amount of p-toluenesulphonic acid required for the conversion of sorafenib base to its tosylate salt may be greater than or equal to the molar equivalent(s) of sorafenib free base used for carrying out the reaction.

In one embodiment, sorafenib free base and p-toluenesulphonic acid may be reacted in 1:1 molar ratio. In another embodiment, sorafenib free base and p-toluenesulphonic acid may be reacted in 1:1.5 molar ratio. In another embodiment, sorafenib free base and p-toluenesulphonic acid may be reacted in 1:2 molar ratio. In another embodiment, sorafenib free base and p-toluenesulphonic acid may be reacted in 1:12 molar ratio. In yet another embodiment, sorafenib base may be reacted with a saturated solution of p-toluenesulphonic acid in water. In a further embodiment, sorafenib free base obtained as a solution directly from a reaction in which sorafenib free base is formed, is reacted with p-toluenesulphonic acid in water as such without isolation.

The term "contacting" may include dissolving, slurrying, stirring or a combination thereof.

The reaction of sorafenib free base with p-toluenesulphonic acid may be carried out at a temperature of about 25° C. to about 100° C.

In one embodiment, the reaction may be carried out at a temperature of about 25° C. to about 35° C. In another embodiment, the reaction may be carried out at a temperature of about 50° C. to about 60° C. In yet another embodiment, the reaction may be carried out at a temperature of about 75° C. to about 85° C.

The reaction mixture may be stirred for about 2 hours to about 20 hours.

In one embodiment, the reaction mixture may be stirred for about 2 hours. In another embodiment, the reaction mixture may be stirred for about 10 hours to 12 hours. In another embodiment, the reaction mixture may be stirred for about 12 hours to 15 hours. In yet another embodiment, the reaction mixture may be stirred for about 15 hours to 18 hours.

Isolation may be accomplished by concentration, precipitation, cooling, filtration or centrifugation, or a combination thereof followed by drying under reduced pressure.

The process of the invention preferably produces sorafenib tosylate of high purity.

In the foregoing section, embodiments are described by way of examples to illustrate the process of the invention. However, this is not intended in any way to limit the scope of the present invention. Several variants of the examples would be evident to persons ordinarily skilled in the art which are within the scope of the present invention.

Methods
XRD
Instrument: Panalytical
Mode: Expert PRO
Detector: Xcelerator
ScanRange: 3-40
Step size: 0.02
Range: 3-40° 2θ
DSC Mettler Toledo instrument
TGA TA instruments (Q 500)

EXAMPLES

Example 1

Preparation of Sorafenib Tosylate

Sorafenib free base (2 g) was added to a saturated solution of p-toluenesulphonic acid (22.0 g) in water (10 mL). The reaction mixture was stirred at about 30° C. to about 32° C. for about 12 hours. The reaction mixture was filtered. The solid material was washed with acetone (2×10 mL) and dried under reduced pressure at about 50° C. for about 12 hours to obtain sorafenib tosylate.
Yield: 44%
HPLC Purity: 98.86%

Example 2

Preparation of Sorafenib Tosylate

Sorafenib free base (3 g) was added to a solution of p-toluenesulphonic acid (14.4 g) in water (6 mL). The reaction mixture was stirred at about 30° C. for about 2 hours. The reaction mixture was filtered, washed with water (2×10 mL) and dried under reduced pressure at about 70° C. for about 12 hours to obtain sorafenib tosylate.
Yield: 85.5%

Example 3

Preparation of Sorafenib Tosylate

Sorafenib free base (2 g) was added to a solution of p-toluenesulphonic acid (1.63 g) in water (10 mL). The reaction mixture was stirred at about 55° C. for about 18 hours. The reaction mixture was filtered and dried under reduced pressure at about 50° C. for about 10 hours to 12 hours to obtain sorafenib tosylate.
Yield: 71.6%

We claim:
1. A process for the preparation of crystalline sorafenib tosylate of Formula I

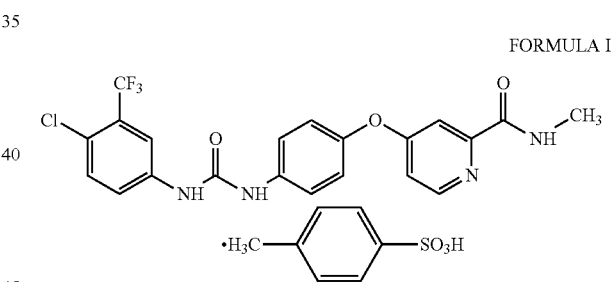

FORMULA I by reacting sorafenib free base with p-toluenesulphonic acid in water, without using any other solvent.

2. The process according to claim 1, wherein sorafenib free base obtained as a solution directly from a reaction in which the sorafenib free base is formed, is used as such without isolation.

3. The process according to claim 1, wherein the sorafenib free base is contacted with 1 mole equivalent of p-toluenesulphonic acid.

4. The process according to claim 1, wherein the sorafenib free base is contacted with 1.5 mole equivalents of p-toluenesulphonic acid.

5. The process according to claim 1, wherein the sorafenib free base is contacted with more than 1 mole equivalent of p-toluenesulphonic acid.

6. The process according to claim 1, wherein the sorafenib free base is contacted with p-toluenesulphonic acid at a temperature of 25° C. to 100° C.

7. The process according to claim 1, wherein the sorafenib free base is contacted with p-toluenesulphonic acid for a period of 2 hours to 20 hours.

8. The process according to claim 1, wherein a saturated solution of p-toluenesulphonic acid in water is used.

\* \* \* \* \*